United States Patent [19]

Bodicky et al.

[11] Patent Number: 4,976,707
[45] Date of Patent: Dec. 11, 1990

[54] FLUID COLLECTION, STORAGE AND INFUSION APPARATUS

[75] Inventors: Raymond O. Bodicky, Oakville; Alan B. Ranford, Creve Couer, both of Mo.

[73] Assignee: Sherwood Medical Company, St. Louis, Mo.

[21] Appl. No.: 190,129

[22] Filed: May 4, 1988

[51] Int. Cl.⁵ .............................................. A61B 19/00
[52] U.S. Cl. .................................. 604/408; 604/410; 604/4; 604/319
[58] Field of Search ....................... 604/408, 410, 4, 6, 604/319, 321

[56] References Cited

U.S. PATENT DOCUMENTS

| Re. 27,132 | 6/1971 | Ilg | 604/410 |
|---|---|---|---|
| 3,328,255 | 6/1967 | Ilg | 167/78 |
| 4,041,944 | 8/1977 | Rhodes | 604/4 |
| 4,270,533 | 6/1981 | Andreas | 604/410 |
| 4,410,358 | 10/1983 | Bennwik et al. | 206/45.34 |
| 4,564,359 | 1/1986 | Ruhland | 604/4 |
| 4,573,992 | 3/1986 | Marx | 604/408 |
| 4,576,603 | 3/1986 | Moss | 604/410 |
| 4,676,775 | 6/1987 | Zolnierczyk et al. | 604/410 |
| 4,735,613 | 4/1988 | Bellin et al. | 604/141 |
| 4,798,578 | 1/1989 | Ranford | 604/4 |

Primary Examiner—Robert A. Hafer
Assistant Examiner—Kerry Owens
Attorney, Agent, or Firm—Stanley N. Garber; Andrew J. Beck; Smith, Montgomery W.

[57] ABSTRACT

A fluid collection, storage and infusion apparatus particularly adapted for collecting, storing and infusing or reinfusing a substance such as blood taken from a patient including a flexible bag-like device having an opposed inlet and outlet, a fluid storage compartment communicating with the inlet and outlet for the collected fluid and a compartment into which a source of fluid such as a gas under pressure can be introduced to exert pressure on the collected fluid to force the fluid out of the fluid storage compartment through the outlet.

12 Claims, 2 Drawing Sheets

U.S. Patent    Dec. 11, 1990    Sheet 1 of 2    4,976,707
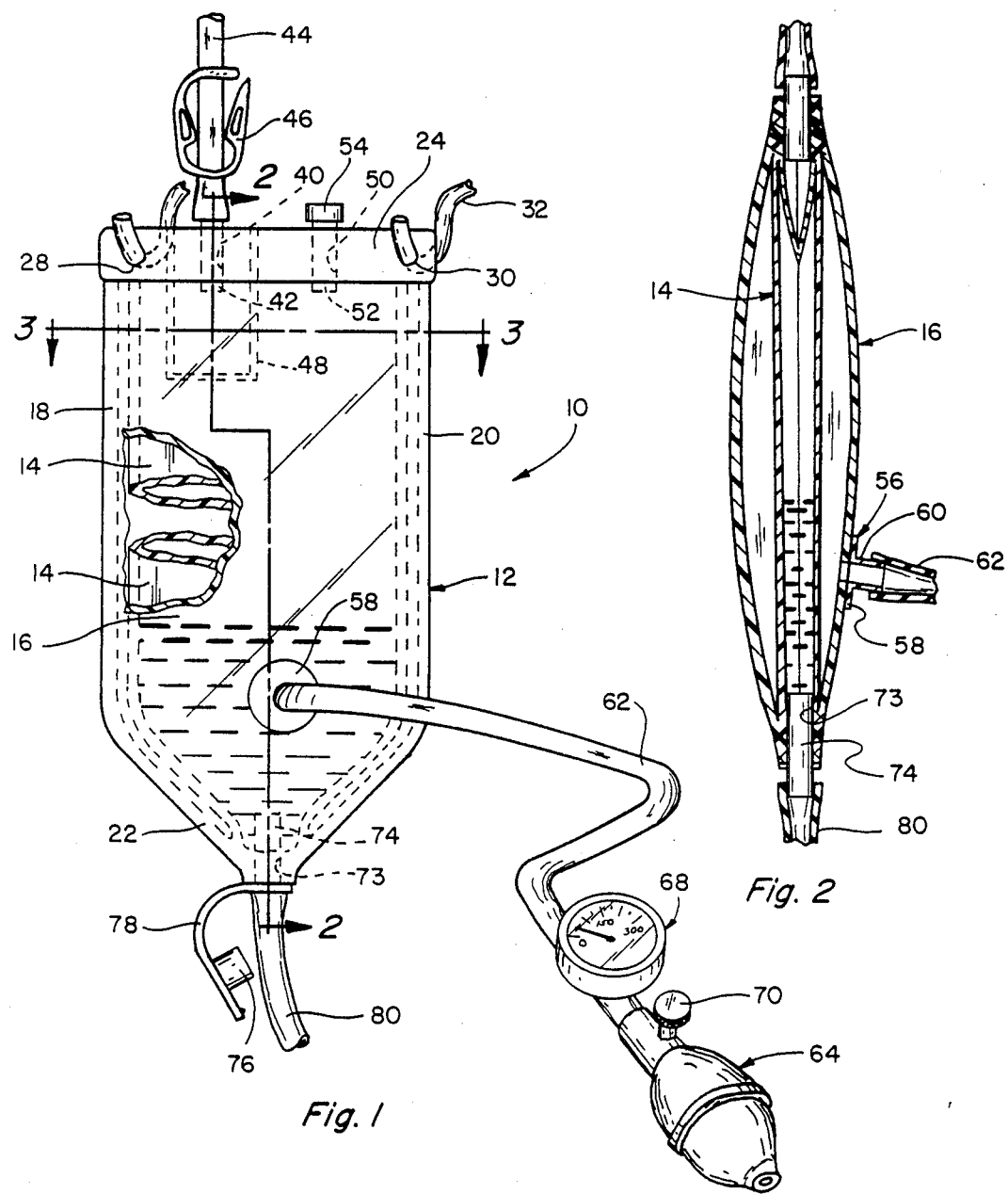
Fig. 1
Fig. 2
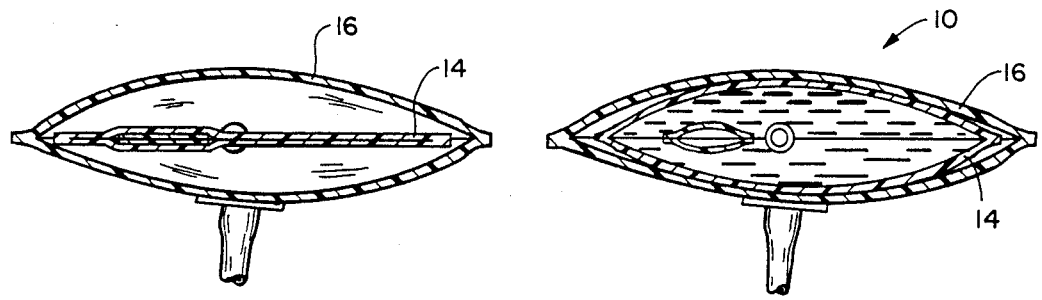
Fig. 3
Fig. 4

FLUID COLLECTION, STORAGE AND INFUSION APPARATUS

BACKGROUND OF THE INVENTION

The present invention relates to a means for collecting, storing and infusing or reinfusing fluids such as blood, and more specifically, to an improved means used to collect, store and/or relatively quickly and efficiently infuse or reinfuse a fluid such as a person's own blood back into the same or into another person.

SUMMARY OF THE INVENTION

The present invention is embodied in a fluid storage and infusion apparatus which overcomes many of the disadvantages, shortcomings and limitations associated with known devices used for the same or similar purposes. The several disclosed embodiments of the present device are relatively simple non-rigid and substantially entirely flexible constructions. Specifically, one embodiment includes an inner flexible and collapsible fluid storage container or bag enclosed within an outer flexible collapsible container. In this construction, both containers are formed of flexible and collapsible materials so that they can be collapsed and placed into relatively small space for storage and handling. Air or gas pressure applied to the outer container will forcibly expel the fluid from the inner container.

In an alternate embodiment of the present invention, the construction is such that instead of one container being within another container, it is formed having a common flexible wall or diaphragm between the flexible walls forming container chambers on opposite sides thereof. This embodiment operates in much the same way as the embodiment described above differing therefrom in that in this case, fluid or gas pressure is introduced for application against one side of the fluid containing portion of the device rather than on all sides thereof. Both embodiments of the present device are substantially totally collapsible and both are used for the same purposes and operate in similar manners.

With the present constructions, fluids such as blood can be stored and can be expelled for infusing into the patient without requiring the bag to be inserted into a second pressurizing device. Also, the entire apparatus of the present device is relatively easy and inexpensive to make and package in sterile condition, and can be utilized without need for a second device for applying pressure to the bag. Thus, the present invention provides a relatively simple device which is easy to use, relatively easy and inexpensive to make, easy to package and store and one which can be operated manually or in association with a source of gas pressure. The present device therefore lends itself to being used in a variety of situations including emergency situations under field conditions as well as in hospitals under emergency or operating room conditions including situations that require the infusing of blood into an injured person or a person being operated on.

Both embodiments of the present device include a filling port for one of the chambers in the subject flexible device. In one embodiment of the present invention as disclosed, an inlet port is located at one end of the device and includes means that communicate it with the inner collection container. An outlet port is also provided and is located to communicate with the opposite end of the inner chamber. When the outlet port is open and the inlet closed, pressure applied within the outer container construction will exert pressure around or against the inner collection container to force the fluid contained therein out through the outlet so that the fluid can be expelled therefrom and infused into a patient or used for some other purpose.

The subject device will also have a second port communicating with the outer container for connection to a source of air or gas pressure including a pump or a device such as to a hand-operated air pump or like device which can be operated manually to force air into the space between the inner and outer flexible containers to collapse the inner fluid containing container and expel the contents thereof. The pressure thus created will cause inflation of the outer container and simultaneous compression of the inner bag thereby causing the fluid in the inner bag to be expelled. If the expelled fluid is blood, it can be infused directly into the patient. Another inlet port, normally sealed closed, can also be provided for operative connection to the inner container so that a suitable anti-coagulant or other medicament can be introduced into the fluid contained therein, if desired.

It can therefore be seen that the present fluid storage and infusion devices are relatively simple structurally, are non-rigid, flexible and fully collapsible, and are relatively easy to manufacture, use, package and store even in a sterile condition and in small space. The present devices can also be constructed of transparent or translucent plastic thereby enabling visual inspection of the contents at all times which is an important advantage for such devices. It is contemplated that the present devices will be used to contain and temporarily store blood taken from a patient and to infuse the blood into the patient as soon as possible or at some later time and without exposing the blood to air or to other contaminants. Further, the present devices can be used to infuse blood or some other fluid taken from the same or from different persons in a manner somewhat similar to known intravenous infusion devices.

It is therefore a principle object of the present invention to provide an apparatus for use in the storage and infusion of fluids such as blood, which device is non-rigid, flexible and collapsible.

Another object is to provide an apparatus for the collection, storage and infusion of fluids which is well suited for emergency medical purposes.

Another object is to provide a device which can expel a fluid such as blood at different rates depending upon the requirements.

Another object is to provide a fluid storage and infusion device which can be operated by gas pressure or manually as by squeezing to expel or assist in expelling fluids therefrom.

Another object is to facilitate handling, storing and dispensing of liquid substances particularly for medical purposes.

Another object is to minimize the time required to infuse blood taken from a patient back to the patient.

Another object is to provide an apparatus for the collection and infusion of blood and other fluids used for medical reasons.

Another object is to provide a fluid storage and infusion device which is of simple and inexpensive construction and is relatively easy to manufacture and package in sterile condition.

Another object is to provide a fluid storage and infusion device which can be constructed of transparent or translucent materials so that the collection and removal or dispensing of fluids therefrom can be visually inspected and monitored.

Another object is to provide a fluid storage and infusion device which lends itself to being stored on emergency vehicles and in emergency medical kits for use in emergency situations.

Another object is to provide a fluid storage and infusion device from which all or substantially all of the fluid contained therein can be expelled Another object is to provide a simple, easy to operate, compact infusion device suitable for hospital, emergency room, operating room and field use.

These and other objects and advantages of the present invention will become apparent to those skilled in the art after considering the following detailed specification of preferred embodiments in conjunction with the accompanying drawings wherein:

BRIEF DESCRIPTION OF THE DRAWINGS

FIG. 1 is a side elevational view of a preferred embodiment of the present invention shown in a partially filled condition and partially cutaway to show in more detail the construction of the inner bag;

FIG. 2 is a cross-sectional view taken along line 2—2 of FIG. 1;

FIG. 3 is a cross-sectional view taken on line 3—3 of FIG. 1 showing the same device in an empty condition after use;

FIG. 4 is a cross-sectional view similar to FIG. 3 showing the device in a substantially filled condition;

DETAILED DESCRIPTION OF THE PREFERRED EMBODIMENTS

Figure 7:
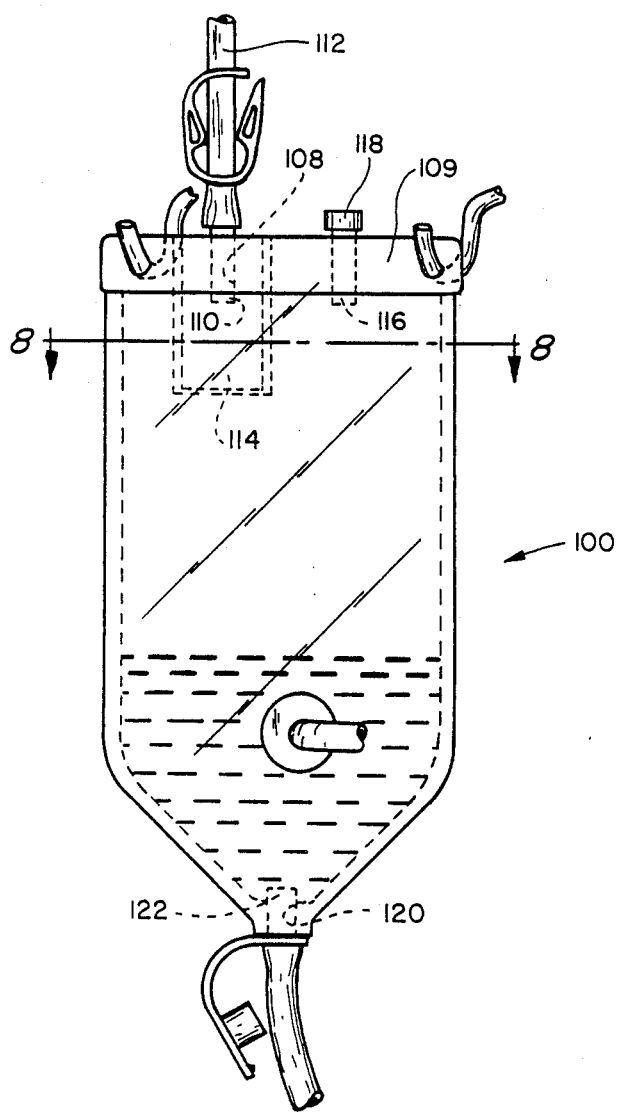
FIG. 7 is a side elevational view of another embodiment of the present invention, said device being shown in a partially filled condition.

Referring to the drawings more particularly by reference numbers, number 10 in FIG. 1 identifies a preferred embodiment of the present fluid collection, storage and infusion apparatus. The apparatus 10 includes a bag structure 12 formed by inner and outer bag portions 14 and 16. The bag portions 14 and 16 are preferably formed of flexible, transparent or translucent sheet plastic material and are of similar size and shape and the material in the outer bag portion 16 is relatively inelastic compared to the material in the inner bag portion 14. The peripheral side portions 18 and 20 of the bags 14 and 16 are preferably not integrally connected so that the spaces on opposite sides of the inner bag 14 communicate. When so formed, and when empty, the bag portions 14 and 16 can be made to be flat and devoid of any space therewithin and therebetween. As shown in FIG. 1, the structure 10 has a V-shaped lower end portion 22 and an upper end edge 24 is shown extending normal to the side edges 18 and 20. The bags at portions 22 and 24 can be made integral by dielectric or heat sealing the bag layers thereat.

The upper bag edge portion 24 is provided with means to enable access to the interior of the inner bag 14 as will be described. The edge portion 24 is also provided with suitable openings such as openings 28 and 30 therethrough for accommodating the end portions of a strap or other hanger means such as the strap 32 which is used to support the bag in suspended condition from an elevated position. The edge portion 24 also has an enlargement which forms an opening or passageway 40 therethrough which communicates with the space or chamber defined in the inner bag 14. The passageway 40 sealably accommodates a tubular member or fitting 42 which is shown sealably connected to one end of flexible tube 44, the opposite end of which may be connected to a device such as to a source of fluid or blood which flows into the inner bag 14. The tube 44 is shown having valve control means 46 thereon to control communication through the tube 44 to the inner bag 14 and to sealably close the tube 44 when desired. The control means may be of known construction. A flexible porous bag-like member or filter 48 extends into the inner bag 14 around the inner open end of the fitting 42 to produce a filtering action on the incoming fluid or blood to prevent undesirable particles from entering the bag.

The upper closed bag end portion 24 has another optional opening 50 that also leads into the inner bag 14 and sealably receives a tubular member 52 positioned thereon. The outer end of the member 52 has a closure member 54 attached thereto which may be of a material that can be pierced by a needle such as on a syringe needle or like device (not shown) and used to introduce an anti-coagulant or other medicament into the inner bag 14, as desired.

The wall of the outer bag 16 is provided with a suitable fitting 56 which has a flange portion 58 with an outwardly extending tubular portion 60 (FIG. 2). The tubular portion 60 sealably receives the end portion of another tube 62 which in turn is shown connected at its opposite end to a flexible bulb assembly 64 which can be squeezed in a usual manner for such devices to introduce air under pressure into the space formed by and between the bag portions 14 and 16. When air is introduced under pressure, it is applied against both opposite surfaces of the spaces defined by and between the bags 14 and 16 to produce pressure between the walls of the bags 14 and 16 to collapse the inner bag 14 and expel the contents thereof. The flexible tube 62 may have a pressure indicating meter or dial gage 68 provided to indicate the amount of applied pressure produced in the space between the bags 14 and 16. Alternatively, the bags 14 and 16 can have their common edges sealed all around their peripheries in which case the inner bag 14 may have to have one or more inwardly extending sealed together portions such as the portion 71 (FIGS. 5 and 6) with an aperture 72 therethrough so that the spaces on opposite sides of the inner bag 14 communicate.

The lower V-shaped end portion 22 of the device 10 has an outlet port 73 through which sealably extends a tubular fitting 74 that communicates the interior of the inner bag 14 with an outlet device such as a device used to feed the fluid or blood contents into a patient. The tubular fitting 74 extends outwardly from the lower end of the bag assembly 10 so that when the bag is suspended as shown in FIG. 1 the contents of the bag can drain out by gravity with or without the help of added pressure between the bag portions. The lower end of the bag is shown also having a closure member 76 attached to a flexible strap 78 and provided to sealably close the lower end of the tube 74 when the device is not in use including when the device is packaged in a sterile condition. However, when the closure member 76 is removed from the lower or outer end of the tubular fitting 74, the end portion of a flexible tubular member 80 can be mounted on the exposed end of the tubular fitting 74 and the opposite end of the tubular member 80 connected to a suitable device such as a device having a cannula needle or like device that can be inserted into a patient's vein when blood is to be infused into the patient.

FIG. 3 is a cross-sectional view of the embodiment of the subject device shown in FIG. 1 when the inner bag 14 is empty after pressure has been introduced into the spaces between the inner and outer bag portions 14 and 16. When the device is in its empty condition before use the walls of the inner and outer bags will be flat against one another. In this condition, which is the condition in which the device is manufactured and packaged, the device occupies relatively little space.

FIG. 4 is a view similar to FIG. 3 but shows the subject device in a substantially filled condition in which case the inner bag 14 extends outwardly over most of its surface into contact with the outer bag 16.

Figure 5:
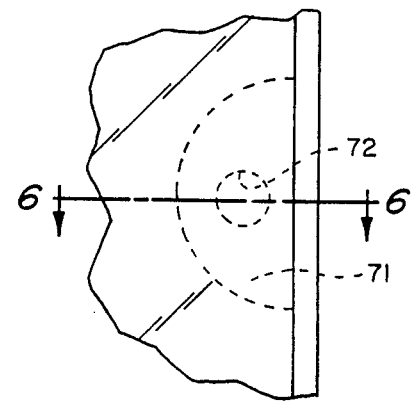
FIG. 5 is a fragmentary side elevational view showing a variation of the device shown in FIG. 1.
Figure 6:
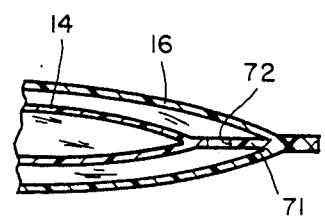
FIG. 6 is a cross-sectional view taken on line 6—6 of FIG. 5.

FIG. 5 and the cross-sectional view in FIGS. 6 taken at the locations shown in FIG. 5 show a variation of the construction shown in FIG. 1 wherein the peripheral edges of both the interior bag 14 and exterior bag 16 are sealed around the peripheral edges thereof and the edge portion of the inner bag 14 at one or more locations is sealed inwardly further as at 71 and the sealed inner bag portions 71 are provided with apertures 72 to provide communication between the spaces on opposite sides of the inner bag.

It is important to note that all forms of the present constructions are relatively simple structurally having a single fluid inlet preferably located at the top when operating and a single fluid outlet at the bottom, and the inlet and outlets can be blocked as required. The present devices are also preferably substantially entirely flexible so that they can be squeezed and/or pressurized to expel the contents thereof thereby providing a simple, easy to operate means for collecting and dispensing fluids such as blood. The optional filter 48 is also helpful to remove particles and clots which otherwise could cause problems. These are important features and advantages especially in a device designed to contain blood and to infuse it into a patient.

Figure 8:
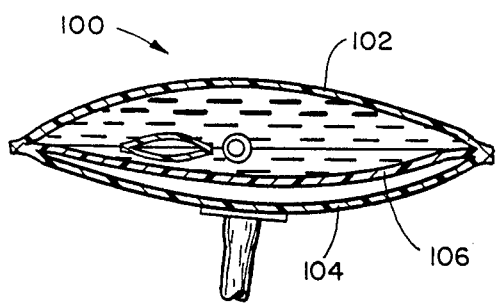
FIG. 8 is a cross-sectional view taken along line 8—8 of FIG. 7 showing the device in a substantially filled condition.
Figure 9:
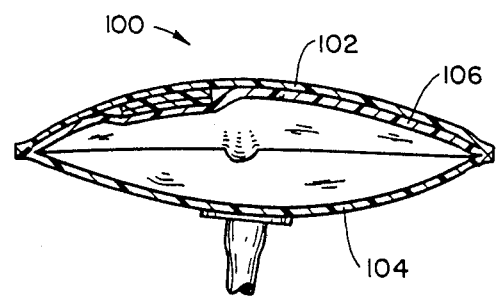
FIG. 9 is cross-sectional view similar to FIG. 8 showing the device in a substantially empty condition.

FIG. 7 shows another embodiment 100 of the subject construction which in most respects is similar to the construction shown in FIGS. 1-4 except that in the construction shown in FIG. 7 the device is constructed to have three instead of four walls. These walls include outer walls 102 and 104 and an intermediate or diaphragm wall 106 therebetween (FIGS. 8 and 9). All the walls 102, 104 and 106 are sealably joined around their peripheries. In the construction 100, a passageway 108 is formed in upper edge portion 109 between the walls 102 and 106 to communicate with the space inside the structure formed by and between these walls. The passage 108 has a tubular fitting 110 sealably positioned therein and in communication with the space defined by and between the walls 102 and 106. The outer end of the fitting 110 is in contact with the end portion of tubular member 112, which is the member through which fluid such as blood enters the subject bag 100. The construction 100 also may have a filter member or filter bag 114 of porous filter material positioned to extend around the inner open end of the tubular fitting 110 to remove foreign particles and substances contained in the incoming fluid and to prevent them from entering the bag and later being expelled. The bag 100, like the bag 10, has another tubular member 116 similar to the tubular member 52 with a cap 118 through which an anti-coagulant or other medicament can be introduced as by being injected into the bag. The tube 116 communicates with the same side of the middle wall 106 as does the tube 110. The structure 100 also has an outlet 120 with an outlet fitting 122 positioned therein.

The bag 100 is sealed completely around its periphery as noted to prevent communication between the spaces on opposite sides of the diaphragm 106. The main difference between the construction 100 and the construction 10 is that rather than having one bag within another as in the construction 10, the wall 106 separates the inside of the bag into two separate chambers on opposite sides thereof, one between the walls 102 and 106 which is used for the accumulation of fluids such as blood, and the other between the walls 104 and 106 which is used for introducing air or other gas under pressure. The walls 102 and 104 in the construction 100 should preferably be relatively stiff compared to the diaphragm 106 so that they form into a rounded but not totally flexible configuration, and the wall or diaphram 106 should be relatively flexible for movement into intimate contact with the walls 102 and 104 to facilitate filling and emptying. Except for these differences, the bags 10 and 100 are similar in construction and operate similarly.

It is apparent that the bags 10 and 100 when used for medical purposes should be made and packaged under sterile conditions, and the various connected walls should be sealed as by dielectric heat sealing to make a strong connection therebetween and prevent leakage. For the most part, the present devices are made of a plastic or plastic-like material which is relatively flexible for ease of manufacture and for ease of storage and handling. The subject bags are also relatively inexpensive to make so that after they are used, they can be disposed of without great loss.

It is contemplated and preferred that the bags 10 and 100 be formed of a translucent or transparent plastic or plastic-like material so that the contents can be observed by the person using them, that is, by the doctor, the nurse, or the technician.

Thus there has been shown and described a novel fluid storage and infusion apparatus which fulfills all the objects and advantages sought therefor. Many changes, modificatons, variations, and other uses and applications of the present device will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A non-rigid bag-like autotransfusion device constructed of flexible wall means defining first and second fluid-tight chambers, said wall means constructed of flexible material so as to substantially completely collapsible in an empty condition in which blood can be collected and stored and from which blood can be dispensed, said wall means including at least three flexible wall members having upper and lower end edge areas sealed together, said first chamber being adapted for collecting blood and said second chamber being adjacent thereto and being adapted to be expanded for expelling blood from said first chamber, said first and second chambers being separated from each other by at least one of said wall members, spaced upper inlet and lower outlet passage means respectively through said upper and lower end edge areas in opposed relation and in fluid communication with the first chamber such that blood enters said first chamber through said upper inlet passage means at said upper end edge area and exits through said lower outlet passage means at said lower end edge area, third passage means communicating with said second chamber for directing pressurized gas thereto for expelling blood from said first chamber, support means in said upper end edge area for freely suspending said autotransfusion device in a vertical condition, first conduit means connected to said inlet passage means for communication with a source of patient's blood to be connected, second conduit means connected to said outlet passage means for infusing the blood, and clamp means positioned on said first conduit means for controlling flow therethrough, said clamp means being movable between different positions to enable or prevent fluid flow therethrough.

2. The non-rigid bag-like autotransfusion device of claim I wherein said flexible wall means defining said first and second fluid-tight chambers comprises four flexible wall members, two of said wall members connected together to form a fluid-tight outer bag the interior of which defines said fluid-tight second chamber, two other of said wall members connected together to form a fluid-tight inner collection bag, the interior of which defines said first fluid-tight chamber, said inner collection bag being fixed within said outer bag.

3. The non-rigid bag-like autotransfusion device of claim 1 wherein said flexible wall members comprise first and second similarly shaped outer wall members the peripheral edges of which are sealingly connected to define an enclosed space therewithin and a third closed wall member positioned between said first and second wall members in said space the peripheral edges of said third wall member being sealingly connected to said peripheral edges of said first and second wall members thereby dividing said space into said first and second chambers on either side of said third wall member.

4. A medical fluid storage and infusion device comprising a fluid-tight flexible outer bag formed of a flexible material having interior and exterior surfaces, spaced opposite side edges and upper and lower end edges, a fluid-tight flexible inner collection bag formed of a flexible material and disposed within said outer bag, said inner collection bag having interior and exterior surfaces, spaced opposite side edges and upper and lower end edges, a fluid-tight expansion space defined between said exterior surface of said inner collection bag and said interior surface of said outer bag, means connecting said upper and lower end edges, respectively, of said outer bag and said inner collection bag, a fluid inlet passage communicating with the interior of said inner collection bag, said first inlet passage being directed through said upper end edges of said outer bag and said inner collection bag for the introduction of fluid into said interior of said inner collection bag, a fluid outlet passage communicating with said interior of said inner collection bag, said fluid outlet passage being directed through said lower end edges of said outer bag and said inner collection bag through which the fluid contents of said inner collection bag can be expelled, and an auxiliary port through said outer bag for the introduction of gas under pressure into said expansion space defined by and between said interior surface of said outer bag and said exterior surface of said inner collection bag for compressing said inner collection bag and thereby expelling the contents of said inner collection bag through said fluid outlet passage.

5. The medical fluid storage and infusion device of claim 4 wherein said flexible material forming said outer bag is less elastic than said flexible material forming said inner collection bag.

6. The medical fluid storage and infusion device of claim 4 further including connecting means connecting said opposite side edges of said inner collection bag, respectively, to said opposite side edges of said outer bag, and gas passage means in said connecting means for gaseous communication between portions of said expansion space on opposite sides of said inner collection bag.

7. The medical fluid storage and infusion device of claim 4 further including filter means positioned within said interior of said inner collection bag and positioned between said fluid inlet passage and said interior of said inner collection bag to filter fluid entering said interior of said inner collection bag through said fluid inlet passage.

8. The medical fluid storage and infusion device of claim 7 further including an auxiliary inlet passage communicating with said interior of said inner collection bag through which an additional substance can be introduced therein.

9. The medical fluid storage and infusion device of claim 8 further including means adjacent said upper end edge of said outer bag for mounting said device in a suspended vertical position.

10. The medical fluid storage and infusion device of claim 9 wherein said outer bag and said inner collection bag are formed from translucent material.

11. The medical fluid storage and infusion device of claim 10 further including a source of gas pressure and means communicating said source to said auxiliary port.

12. The medical fluid storage and infusion device of claim 11 further including a flexible tubular member connected to communicate with said fluid inlet passage, and means to control fluid flow through said flexible tubular member.

* * * * *